US00PP31587P2

(12) United States Plant Patent
Hansen

(10) Patent No.: US PP31,587 P2
(45) Date of Patent: Mar. 24, 2020

(54) ***HIBISCUS* PLANT NAMED 'SUMMER CARNIVAL'**

(50) Latin Name: ***Hibiscus* hybrid (L.)**
Varietal Denomination: Summer Carnival

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,348

(22) Filed: Nov. 5, 2018

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 6/60; A01H 5/02
See application file for complete search history.

*Primary Examiner* — Keith O. Robinson

(57) ABSTRACT

A new and distinct cultivar of winter-hardy, herbaceous, perennial, hybrid *Hibiscus* plant named 'Summer Carnival' comprising an upright habit of multiple, well-branched, basal stems producing flowers near the top of the plant. Flowers are hot cerise, and the calyces display light green sepal centers and pale yellow margins while in bud and after flower drop. The foliage is primarily three-lobed, deeply incised, and grayish-green with creamy irregular margins frequently blushed with reddish purple. The stems exposed to high ultraviolet light develop reddish coloration.

2 Drawing Sheets

Botanical classification: *Hibiscus* hybrid (L.).
Variety denomination: 'Summer Carnival'.

STATEMENT REGARDING PRIOR DISCLOSURES UNDER 37 CFR 1.77(b)(6)

The first public disclosure of the claimed plant, in the form of a sale, was made by Walters Gardens, Inc. on Nov. 27, 2017. The new plant was then sold to the public through Plant Delights Nursery, Inc. Walters Gardens, Inc. obtained the new plant and all information relating thereto, from the inventor. No plants of *Hibiscus* 'Summer Carnival' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'Summer Carnival' discovered by the inventor on Aug. 10, 2014 in the research fields of a wholesale perennial nursery in Zeeland, Mich. The new plant is a branch chimeral sport selected from an unnamed unreleased proprietary seedling. During the trial process the new plant was assigned the breeder code labeled 14-SP-HIB-317. Both parents have a complex mixture of species in them, comprising the species: *moscheutos* and *coccineus*. *Hibiscus* 'Summer Carnival' was first asexually propagated by shoot tip cuttings on Aug. 10, 2014 and later by sterile shoot-tip tissue culture at the same nursery in Zeeland, Mich. The resultant asexually propagated plants have been found to be stable and true to type in successive generations of asexual reproduction.

BRIEF SUMMARY OF THE PLANT

*Hibiscus* 'Summer Carnival' differs from its parents as well as all other hardy herbaceous *Hibiscus* known to the applicant in distinct traits. The two parents that produced the original plant that formed the branch chimeral sport have not been maintained, nor have photographs been maintain, so no comparison can be made with these two parents other than they had no variegation in the foliage. The most similar *Hibiscus* in flower color known to the applicant are *Hibiscus* 'Sultry Kiss' U.S. Plant Pat. No. 22,300 and *Hibiscus* 'Summer in Paradise' U.S. Plant Pat. No. 28,730. 'Sultry Kiss' has flowers that are slightly deeper reddish color. 'Summer in Paradise' is shorter in habit, and 'Sultry Kiss' is taller and broader in habit than the new plant. Both 'Sultry Kiss' and 'Summer in Paradise' have flower petals that are more overlapping than the new plant, but neither have the variegated margin of the new plant. The most similar plant known to exist to the applicant in habit and leaf form is 'Plum Fantasy' U.S. Plant Pat. No. 25,986, but 'Plum Fantasy' has a slightly more cupped flower of a different color, is slightly taller and broader in habit, and the foliage lacks the marginal variegation of the new plant. *Hibiscus syriacus* 'America Irene Scott' U.S. Plant Pat. No. 20,579 has yellowish marginal-variegated foliage and double pink flowers but it is not herbaceous, nor does the variegation produce the nice reddish-purple blushing in the creamy margin.

The original mutated parent was not maintained and therefore no comparison of the new plant to the parent is possible, however the mutation parent had no variegated foliage, but similar is most other characteristic and identical in flower color.

*Hibiscus* 'Summer Carnival' is a unique hardy herbaceous *Hibiscus* with the following combined traits:

1. Winter-hardy, perennial with upright habit of multiple, well-branched, basal stems.
2. Many rotate flowers of hot cerise produced near the top of plant.

3. Flower buds are distinctly variegated grayish-green with creamy margins along entire length of sepals.
4. Grayish-green, deeply-incised, primarily tri-lobed foliage with an irregular creamy margin frequently blushed with reddish-purple.
5. Stems exposed to high ultraviolet light develop reddish stems.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
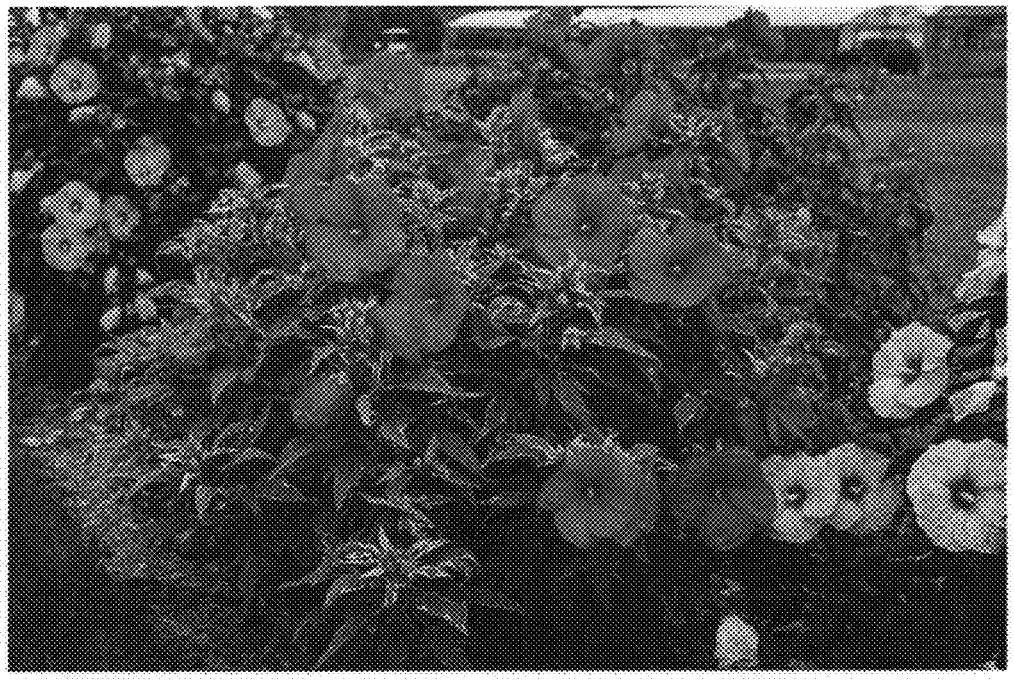
FIG. 1 shows a three-year-old plant in full flower in a trial garden.
Figure 2:
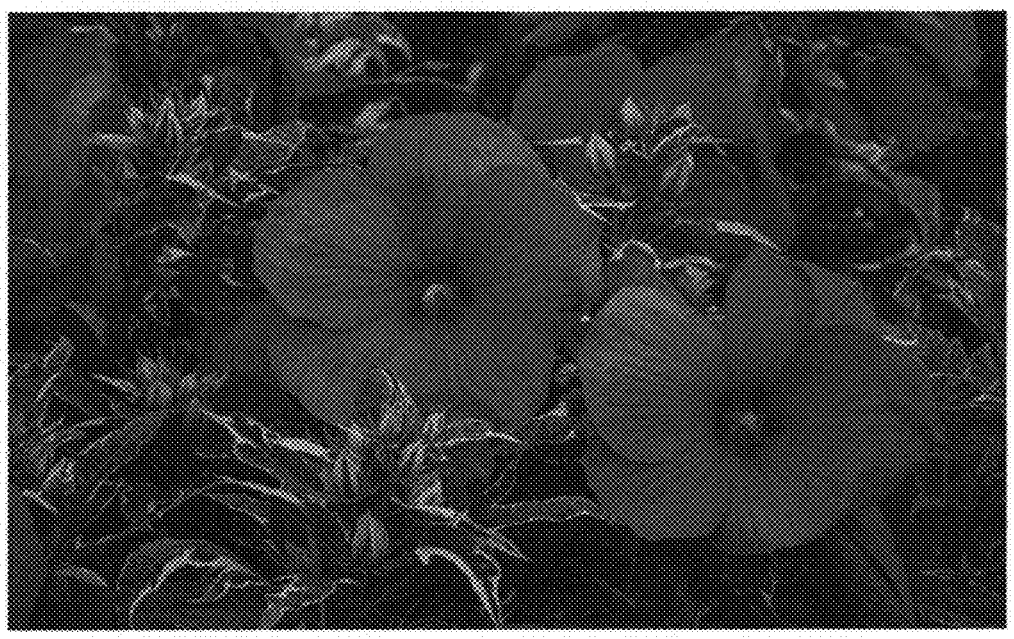
FIG. 2 shows a close-up of the flower.
Figure 3:
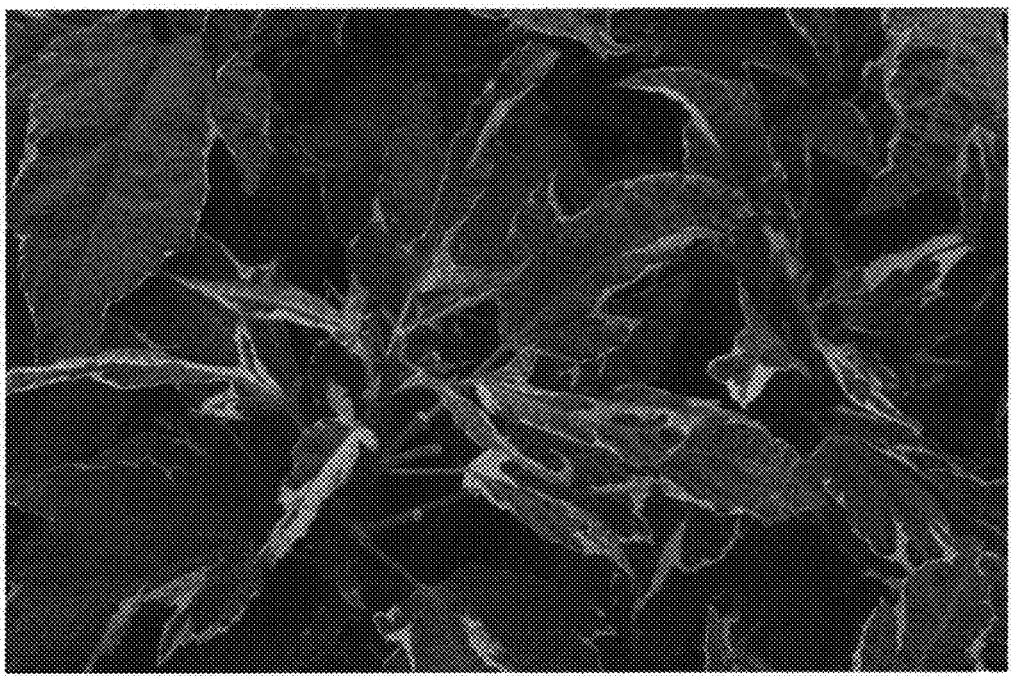
FIG. 3 shows a close-up of the foliage with variegation.
Figure 4:
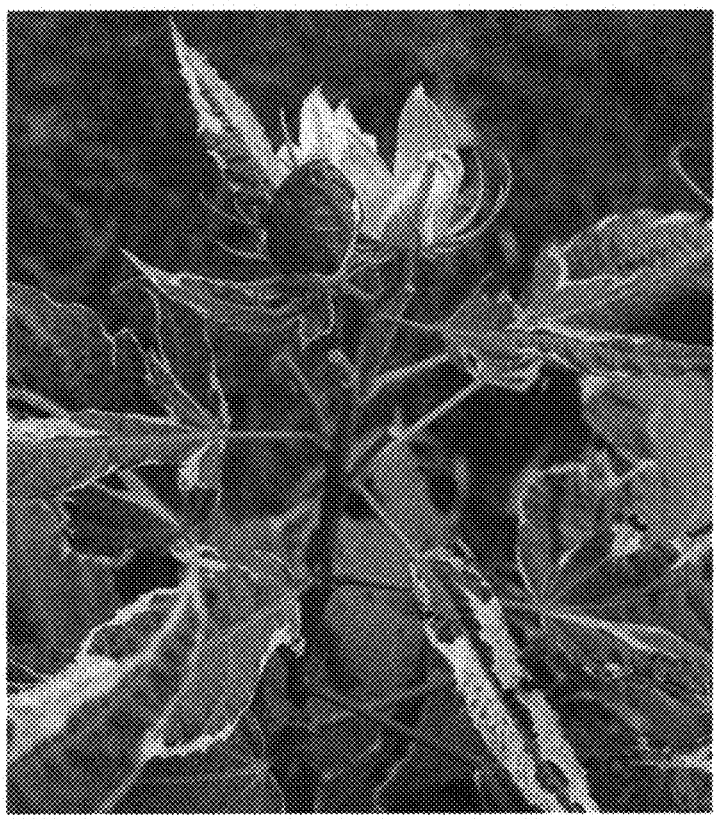
FIG. 4 shows flower bud and the reddish stems developed when exposed to high ultraviolet light.

The following descriptions and color references are based on the 2015 edition of The Royal Horticultural Society Colour Chart except where common dictionary terms are used. The new plant, *Hibiscus* 'Summer Carnival', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: The branch chimeral sport parent is an unreleased, unnamed proprietary seedling of two unreleased, proprietary parents (both not patented);

Propagation:

*Method*.—Stem cuttings and sterile shoot-tip plant tissue culture division.

*Time to initiate roots from tissue culture*.—About two weeks.

*Rooting habit*.—Normal, branching, developing thick to about 2.2 cm diameter, fleshy; root color creamy yellow between RHS 161D and lighter than RHS 159D depending on soil type.

*Crop time*.—Under normal summer growing conditions 12 to 16 weeks to flower in a four-liter container from cutting. Plant vigor is very good.

Plant description:

*Plant habit*.—Winter-hardy herbaceous perennial with about 40 thick upright and heavily branched main stems producing an upright spreading mound to about 133.0 cm tall and about 185.0 cm wide; with up to 15 branches per main stem, average about 8 primary branches per main stem protruding at about 45° from horizontal; flowering in the top 65.0 cm of plant with up to about 46 flowers per main stem, average flowers per stem about 30.

*Stem*.—Terete, glabrous, glaucous; to about 133.0 cm tall and about 22.0 mm diameter at base, average about 122.0 cm tall and about 18.0 mm diameter at base.

*Stem color*.—Variable, proximal two-thirds nearest RHS 138B with irregular longitudinal streaks of nearest RHS 158C, distally with more ultraviolet light exposure nearest RHS 182C to nearest RHS 183D.

*Lateral branches*.—Average about 8 per stem; terete, glabrous, glaucous; to about 50.0 cm long and 8.0 mm diameter, smaller distally.

*Lateral branch color*.—Variable with light exposure from RHS 146D in low light to RHS 182C in moderate light and RHS 182A in higher light.

*Internode*.—About 5 nodes per stem below branches and 26 total nodes below flowers; average internode length about 3.6 cm on unpinched plant.

*Internode color*.—Same as surrounding stem; in proximal two-thirds nearest RHS 138B with irregular longitudinal streaks of nearest RHS 158C, distally with more ultraviolet light exposure nearest RHS 182C to nearest RHS 183D.

Foliage description: Alternate; ovate; coarsely and irregularly dentate; apex and side lobes acute; base rounded; glabrous abaxial and adaxial; moderately incised one-third of way to petiole; trilobate; slightly lustrous adaxial surface, matte abaxial surface; leaf blades to about 21.0 cm long and about 13.8 cm across, average blade size 12.5 cm long and 7.0 cm wide; variegated with irregular width between 0.5 mm and 4.5 mm of creamy margin sometimes tinted deeply with reddish purple; no fragrance detected; lobing medium.

*Foliage color*.—Young expanding leaves — adaxial nearest blend between RHS N138A and RHS 191B with margin of variable blushing of nearest RHS N187D to RHS 59C, abaxial nearest RHS 148C with margin of nearest RHS 155A with variable blushing, but fainter than adaxial, of nearest 59C; distal mature leaves — adaxial nearest RHS N138A with margins of nearest RHS NN155B with variable and irregular blushing of nearest RHS 187C to RHS N187C, abaxial nearest RHS 148C with margins of nearest RHS NN155A and variable and irregularly blushing on margins of nearest RHS 59C.

*Veins*.—Palmate; glabrous, slightly glaucous, matte surface abaxial and adaxial; costate on abaxial.

*Vein color*.—Young adaxial nearest RHS N138D with faint tinting of nearest RHS 185D, young abaxial nearest RHS 155A with faint tinting of nearest RHS 186C; mature adaxial nearest RHS 147C with some proximal blushing of nearest RHS 187C, mature abaxial nearest RHS 155A with faint tinting of nearest RHS 186C.

*Petioles*.—Mostly cylindrical, proximally slightly applanate on adaxial side near base; glaucous; glabrous; to about 12.5 cm long and 5.5 mm diameter at base, average size about 8.5 cm long and 4.5 mm wide at base.

*Petiole color*.—On young expanding leaves adaxial between RHS 51B and RHS 51C, abaxial between RHS N148D in lower light and RHS 51D in higher light intensity; on mature leaves adaxial between RHS 181D and RHS 181C, abaxial or adaxial in protection from heavy light between RHS 145A and RHS 146D.

Flower description: Complete; actinomophic; upward to outward facing; rotate; lasting up to two days on plant; no fragrance detected;

*Buds one day prior to opening*.—Oblong with acute apex and bluntly rounded base; sepals mostly adpressed to petals, carinate at sepal fusions; about 6.5 cm long and about 3.0 cm diameter at middle.

*Bud color*.—Exposed petal color nearest RHS 59B.

*Epicalyx*.—Typically 10 to 11 per flower; linear; margin entire and micro-ciliolate, glabrous; dull surface abaxial and adaxial; narrowly acute apex and truncate base, arcuate upwards near apex; about 3.3 cm long and base of about 3.0 mm wide.

*Epicalyx color*.—Adaxial and abaxial blend between RHS 146D and RHS 148D, rarely nearest RHS 155D.

*Calyx*.—Fused in basal 1.7 cm to form star-shaped hypanthium about 5.1 cm across and 3.5 cm deep; persist after flower dehiscence.

*Sepals*.—Five; acute apex; glabrous; margin entire, edentate, variegated to width of about 4.0 mm wide; abaxial and adaxial surfaces matte; about 3.5 cm long, about 10.0 mm wide at fusion.

*Sepal color*.—Adaxial center between RHS 145C and RHS 145B and margins nearest RHS NN155B; abaxial center lighter than RHS 146D and margins nearest RHS NN155C; veins not apparent, same as surrounding tissue.

*Flowers*.—Solitary, up to 40 per main stem without pinching; slightly cupped petals; mostly outwardly facing; natural spread to about 16.0 cm across and 5.0 cm deep from center to edge of petals; smaller in later season; with lustrous red eye nearest RHS 59B about 3.5 cm across; persist for one to two days; effective for at least 8 weeks beginning early August; no detectable fragrance.

*Petals*.—Five; microscopically puberulent abaxial and adaxial, glabrous eye; adnate to the androecium to form a column, imbricate to about 50% overlapping at widest part (petals overlapping to 50% of the petals on either side); veins longitudinal, primary and secondary veins slightly impressed on adaxial and costate abaxial; petal shape: rounded with distinct claw and limb; margins: entire, edentate; apex: rounded; base: short claw-like; size: average about 9.2 cm across and about 9.5 cm long, claw base about 7.0 mm across (larger in earlier part of flowering season); undulation weak.

*Petal color*.—Adaxial between RHS 60C and RHS 59C with eye nearest RHS 59B, and veins in longitudinal center near RHS 59C; abaxial between RHS 53C and RHS 60C with veins between RHS 53B and RH 53C.

*Gynoecium*.—Single; partially enclosed in column; Column: glabrous except base micro-puberulent, lustrous; about 5.2 cm long and base about 6.0 mm across; with pistil protruding about 8.0 mm; Column color: nearest RHS 56C with longitudinal streaks of nearest RHS, distally between RHS 46B and RHS 46C; Style: micro-puberulent in region above column; about 4.0 cm long, penta-furcate in about distal 7.0 mm; branch diameter about 1.0 mm; color nearest RHS 46B; Stigma: typically five; flattened globose, puberulent, about 1.5 mm in diameter and 1.0 mm tall; color nearest RHS 53A; Ovary: superior, semi-globose, rounded apex and flat base; about 8.0 mm across at base and about 7.0 mm tall; acute apex; color typically between RHS 145B and RHS 145C, rarely longitudinally striated with blend between RHS 153D and RHS 162D.

*Androecium*.—Filaments: numerous, about 100; about 3.5 mm long and about 0.3 mm diameter; attached along nearly the entire length of column; color nearest RHS 56D with a light tint of nearest RHS 46C; Anthers: flattened ellipsoid; dorsifixed; about 2.0 mm long and 1.50 mm across and about 0.8 mm thick; color nearest RHS 158B; Pollen: abundant, globose, less than 0.1 mm long; color nearest RHS 8A.

Pedicel: Cylindrical, glabrous, glaucous; length from base of sepal to abscission point about 12.0 mm long, from abscission point to stem node average about 4.0 cm long; about 3.0 mm wide; longer on early flowers and decreasing in distal flowers; color variable depending on light exposure, nearest RHS 146D protected from high light exposure and nearest RHS 181C in high light exposure;

Peduncle: Cylindrical, glabrous, glaucous; flowering in the distal 50.0 cm; color nearest RHS 184B;

Fruit: Penta-loculicidal capsule; pubescent along inner septa, glabrous outside; nearly globose, slightly cuspidate apex and flattened base; about 12.0 mm long and 12.0 mm diameter; color nearest RHS N199B when mature;

Seed: Minutely floccose; globose; about 1.5 mm in diameter; color nearest RHS N200A;

Resistance: *Hibiscus* 'Summer Carnival' has not displayed any pest and disease resistance beyond that typical of hardy perennial *Hibiscus*. The new plant has not shown susceptibility to any form of leaf spot, root rot, or stem blight but may shown typical susceptibility to *Atomacera decepta*.

Growth requirements: The plant grows best with plenty of moisture. Hardiness is at least from USDA zone 4 through 9.

I claim:

1. A new cultivar of hardy herbaceous perennial *Hibiscus* hybrid plant named 'Summer Carnival' as herein illustrated and described.

* * * * *